United States Patent [19]

Krueger

[11] Patent Number: 4,677,968
[45] Date of Patent: Jul. 7, 1987

[54] METHODS OF TESTING THE REACTION OF VARIOUS SUBSTANCES ON LIVING HUMAN SKIN

[75] Inventor: Gerald G. Krueger, Salt Lake City, Utah

[73] Assignee: University of Utah Research Foundation, Salt Lake City, Utah

[21] Appl. No.: 818,871

[22] Filed: Jan. 14, 1986

[51] Int. Cl.$^4$ .............................................. A61B 19/00
[52] U.S. Cl. ........................................ 128/1 R; 424/3
[58] Field of Search ................... 128/1 R; 623/11, 15; 435/6, 29; 424/3

[56] References Cited

PUBLICATIONS

Krueger et al., "The Development of a Rat/Human Skin Flap Served by a Defined And Accessible Vaculature on a Congentially Athymic (Nude) Rat," Journal of Fundamental and Applied Toxicology, (submitted for publication in Journal of Fundamental and Applied Toxicology).
Pershing et al., "Enhanced Percutaneous Absorption of Benzoic Acid Across a Nude Rat Skin Sandwich Flap Following Phenylephrine Induced Vasoconstriction," 34 Clinical Research 163A (Jan. 1986).
Krueger et al., "The Development of Rat/Human Skin Flap Served by a Defined and Accessible Vasculature on an Athymic Rat," Fifth Annual Chemical Defense Bioscience Review (May 29–31, 1985).
Wojciechowski et al., "A Study of Human Skin Grafts on Congenitally Athymic (Nude) Rats," 33 Clinical Research 298A (Apr. 1985).
Burton, et al., "Comparison of In Vivo And In Vitro Transdermal Drug Absorption and Dermal Drug Metabolism of Vidarabine Using a Unique Isolated Skin Flap Model," 33 Clinical Research 628A (Apr. 1985).
Krueger, "Feasibility of Human Skin Grafts on an Isolated but Accessible Vascular Supply on Athymic Rats as a System to Study Percutaneous Penetration and Cutaneous Injury," Department of the Army Annual Report (Nov. 1984).
Wojciechowski et al., "Skin on an Isolated Accessible Vaculature as a Model System to Study Skin Pathophysiology", 32 Clinical Research 482A (Apr. 1984).
Burton, et al., "Transcutaneous Absorption of Benzoic Acid in a Unique Isolated Skin Flap Model", 32 Clinical Research 17A (Feb. 1984).
Wojciechowski, "A Grafted Skin Flap on an Isolated Accessible Vasculature as a Model System to Study the Skin Pathophysiology", 32 Clinical Research 18A (Feb. 1984).
Burton et al., "Transcutaneous Absorption of Benzoic Acid in a Unique Isolated Skin Flap Model", 32 Clinical Research 574A (Apr. 1984).
Krueger et al., "The Nude Mouse in the Biology and Pathology of Skin," The Nude Mouse in Experimental and Clinical Research, vol. 2, (1982).
Krueger "The Nude Mouse in Dermatology," 12 Progress in Dermatology 17, (Jul. 1978).
Cubie H. A., "Failure to Produce Warts on Human Skin Grafts on Nude Mice" in *British J. of Derm.* Jun. 1976, 94(6) p. 659–665.
Yuspa et al., "Maintainence of Human Skin on Nude Mice for Studies of Chemical Carcinogenesis", in *Cancer Lett.* Apr. 1979 6(4–5) p. 301–310.
Sabo et al., "Split Thickness Skin Grafts–An Experimental Study of Factors Related to Ease or Difficulty of Procuring Satisfactory Grafts of Skin from Mice MCA and Some Common Laboratory Animals", *J. Dermatol Surg. Oncol.,* Oct. 1978, 4(10) p. 770–772.

*Primary Examiner*—C. Fred Rosenbaum
*Assistant Examiner*—Jerome R. Smith, Jr.
*Attorney, Agent, or Firm*—Workman, Nydegger & Jensen

[57] ABSTRACT

Methods and testing models for use in testing the effects of substances on human skin without the need for human subjects. The present invention includes a flap having viable, functional human skin on one side and animal skin on the opposite side. Sandwiched between the layers of skin are one or more isolated veins, arteries, and nerves. This isolated vasculature joins the animal and the skin flap. The human skin layer is simply a split thickness skin graft prepared from living, but discarded, human skin. The present invention allows various substances to be applied directly to the human skin. The presence of absence of the substance can then be detected in the blood flowing in the isolated vasculature. Thus, tests involving living human skin can be performed without the need to directly involve human subjects.

36 Claims, 1 Drawing Figure

FIG. 1

METHODS OF TESTING THE REACTION OF VARIOUS SUBSTANCES ON LIVING HUMAN SKIN

BACKGROUND OF THE INVENTION

1. The Field of the Invention

This invention relates generally to methods for testing reactions of substances on human skin. In particular, the present invention relates to such testing methods which are capable of using living human skin to test the properties of various substances and medicaments without directly involving a human subject.

2. Description of the Art

The behavior of human skin in various environments and its reaction to chemicals of all types is of particular interest in medicine and other related areas of technology. This is true because of the importance of the skin in performing a wide range of functions critical to the maintenance and well being of the human organism as a whole.

The primary functions of skin are to provide the body with protection and to maintain a constant environment for the organism. The skin protects the body against the influence of mechanical, thermal, chemical, and electrochemical agents encountered in the environment, and it also protects the body against the invasion of microorganisms.

The skin regulates body temperature by sweat secretion and by varying the circulation of the blood through the skin. The skin acts as a housing for the neurosensory organs critical to the senses of touch, cold, heat, and pain. The skin provides a site for the synthesis of various substances, including vitamin D, and also functions to prevent the body from losing excessive amounts of fluids, heat, and the like. The critical importance of the skin can be readily appreciated by the numerous important functions performed by the skin.

Because of the importance of the skin in protecting an individual from the environment and in performing other critical functions, the study of the skin in an important area of medical science. The study of the skin clearly has the potential of providing additional insights into the mechanism of disease and the nature of the reaction between harmful agents and the body. An understanding of the interaction of skin with various toxic agents, including carcinogens, is important to the understanding of disease functions and methods for preventing disease. Study of the interaction of the skin and the environment also provides insight into the characteristics of a safe and healthy environment.

In understanding the function of the skin and the reaction of substances in the environment with the skin, it is apparent that the study of the penetration of the skin by various substances is important. It is generally found, as would be expected, that smaller molecules can penetrate the skin faster than larger ones.

Furthermore, non-ionized molecules are more effective in penetrating the skin than are ionized compounds. Finally, it has been found that very large molecules such as proteins and polysaccharides penetrate the skin very slowly. However, beyond the generalities mentioned above, it would be desirable to perform actual tests on the skin in situ in order to come to a full understanding as to the action of any particular molecule on the skin.

Several different approaches have been developed for testing the effects of substances in contact with the skin. One such method involves simply placing a quantity of the substance to be tested on the skin of a human subject. At a predetermined time later, a sample of body fluid, such as urine or blood, is extracted and analyzed. From the resulting analysis, some understanding can be gained of the ability of the substance to penetrate the skin.

Several disadvantages are apparent when employing such a method of testing. One obvious problem is that when testing potentially harmful agents, including new pharmaceuticals, toxic substances, or carcinogens, it is not ethical or proper to use a living human subject. The danger of harm to the human subject is simply too great.

Even if problems generally related to safety could be ignored, testing using human subject still has serious difficulties. One primary difficulty is that the accuracy of the test is extremely limited. For example, the substance to be tested must penetrate the skin and then enter the blood stream. Once the substance enters the blood stream it will pass through the kidneys, the liver, and other internal organs. These organs will tend to sweep the impurity out of the blood stream. In addition, it is found that various mechanisms within the skin itself may remove the substance, so that it is difficult to obtain an accurate indication of the actual absorption of the substance by the skin.

In order to overcome the problem of administering potentially harmful substances to human subjects, tests on animals have often been substituted. As would be expected, in addition to the problems discussed above, difficulties are encountered in animal tests because of the extreme differences between animal skin and human skin. Some of the differences include the differences in thickness of the skin, differences hair density, and differences in the number of sebaceous and eccrine glands.

It has been found that the skin of the domestic pig most closely approaches human skin. However, even pig skin is substantially different from human skin, and test results obtained on pigs cannot necessarily be directly correlated to humans.

Because of the problems described above in testing substances on live human subjects and on animal subjects, researchers have developed other test methods. One widely used testing method simply involves a sample of dead skin removed from a human subject. The skin is placed in a test apparatus where the desired test substance is placed on the skin and its penetration through the dead skin sample is measured. Essentially a controlled amount of the substance is placed on top of the sample and the presence of the substance below the sample is subsequently measured.

In order to use the results of this test method, it is generally necessary to make the assumption that dead skin behaves in the same manner as living skin and that the effects of circulation through the skin are negligible. This assumption, however, is manifestly incorrect. Living skin dynamically removes substances which enter through the skin surface. Thus, the effect of blood flow through the living skin, as well as many other factors, make test results using dead skin samples unpredictable when correlated to living subjects.

Thus, the art is presently lacking an adequate system for testing the reaction of substances on the skin. In particular, there exists no satisfactory method for testing the action of substances on living human skin. As discussed above, animal experiments and experiments with dead human skin do not provide satisfactory results.

The art is lacking testing methods which facilitate the study of the metabolic capacity of the skin, the interaction of the skin with toxic substances, and the study of the skin as a barrier to the delivery of pharmaceuticals. Such testing methods could provide an understanding of the reaction of the skin with various drugs in order to study the potential for systemic drug delivery through the skin. For example, such testing methods could provide insight into the administration of medicaments using iontophoresis and other similar noninvasive administration techniques.

An adequate testing method would provide a method for studying the metabolism of hormones, cytokins, or other substances in the skin and could provide additional insight into the inflammatory processes. In addition, an adequate testing method using the microcirculation of the skin would be helpful in understanding the distribution of various agents through the microcirculatory system. This would aid in defining the role of microcirculation through the skin in overall physiological processes.

Thus, what is needed in the art are improved methods and experimental models and testing the reaction of substances on the human skin. In particular, what is needed in the art are methods and testing models for testing the reaction of substances with living human skin. It would be a further advancement in the art to provide such methods and apparatus which would allow a researcher to directly access the blood supply to a skin sample. Specifically, it would be an advancement in the art to provide such testing methods and models which would provide for the testing of blood directly below the skin, without allowing the blood to first travel through the organism as a whole.

Such methods and testing models are disclosed and claimed herein.

BRIEF SUMMARY AND OBJECTS OF THE INVENTION

The present invention relates to testing models and methods for their use in testing the reaction of substances directly on human skin, without the use of a human subject. As mentioned above, presently available methods for testing the reaction of pharmaceuticals and other substances on human skin are inadequate at best. Since it is generally impossible to use human subjects, existing systems fail to allow for the testing of drugs directly on living human skin. Thus, existing systems are reduced to either using animal subjects or to using dead human skin for testing and analysis. The present invention overcomes these limitations of the existing art.

In the present invention, an isolated neurovascular island skin flap is produced on a test animal. On one side of the flap is a human skin graft, and on the other side of the flap is a layer of animal skin. Skin other than human skin may also be used, if desired.

The isolated skin flap is produced by a surgical procedure performed on the test animal. It has been found that athymic rats and mice are desirable test animals because of their generally hairless state. Generally an area of the skin in the abdominal region of a test animal is isolated.

In one embodiment of the present invention, an area of skin served by the epigastric blood vessels is isolated by making incisions along three sides of the subject area to form a skin flap. Simultaneously, a split thickness skin graft (hereinafter sometimes referred to as "STSG") of human skin is obtained. The human STSG is of approximately the same size and configuration as the skin flap created on the abdomen of the test animal. The STSG of human skin is then surgically attached to the subcutaneous surface of the isolated flap area of animal skin sandwiching between the two layers of skin the vasculature formerly serving the animal skin.

In practice, it has been found desirable to leave the resulting flap attached to the abdominal area of the test animal until the human skin and the affected area of animal skin have grown together to form an integral flap. After this healing period, the flap is moved to the dorsal side of the animal through a subcutaneous tunnel. During this procedure, the vasculature supplying the flap is totally isolated. Other methods, of course, are possible in order to isolate the flap; however, the removal of a flap to the dorsal side of the animal has been found to be desirable in order to protect the flap and in order to facilitate testing.

Since the flap is supplied by isolated blood vessels, the vasculature supplying the flap can be directly accessed. Thus, blood samples can be extracted from this vasculature and analyzed for the presence of various substances before the blood travels through the remainder of the animal's organs. This provides essentially direct access to substances penetrating the human skin layer.

In testing, the substance to be tested can be placed on the flap using a half-cell diffusion chamber or by using direct disposition on the skin. The substance then reacts with the skin and/or is absorbed by the skin. The absorption of the material by the skin can then be detected directly by extracting and analyzing the blood flowing out of the flap area.

This testing model provides a method whereby the presence of the substance to be tested can be directly measured. In contrast to prior testing methods, the present method allows the blood to be tested before it circulates through the animal and before the substance is potentially removed by the liver, kidneys or other organs. In addition, the reaction of the substance with living human skin, as opposed to dead skin used in some existing procedures, can be directly analyzed and controlled. Thus, the major drawbacks of existing testing methods are overcome in the present invention.

As a result, it is a general object of the present invention to provide improved methods for testing the reaction of various substances on living human skin.

It is a further object of the present invention to create a viable human/animal skin flap which may be used in determining the effects and responses of substances on human skin.

It is a related object of the present invention to provide such a human/animal skin flap which is served by isolated vasculature such that blood samples can be obtained directly from the skin flap.

It is an additional object of the present invention to provide methods for testing the reaction of various substances on skin whereby the presence of the substance can be detected after it penetrates the skin but before it enters the general blood stream of the test animal.

It is also an object of the present invention to provide methods for performing tests on living human skin without directly using human subjects.

These and other objects and advantages of the present invention will become apparent upon reading the following description and appended claims and upon reference to the drawing.

DETAILED DESCRIPTION OF THE PREFERRED EMBODIMENTS

The present invention is related generally to methods for testing the effects of various substances, including pharmaceuticals and other medicaments on human skin. The invention is also related to an experimental structure or model which provides a living human skin surface for use in testing procedures. The experimental structure is generally a living skip flap having animal skin on one side and human skin on the opposite side. Sandwiched between the two layers of skin is an isolated vascular pedicle consisting generally of a single artery, vein, and nerve. This vascular pedicle is, in turn, in direct communication with the remaining vasculature of the test animal.

As discussed previously, existing methods and apparatus for testing the reaction of substances, such as pharmaceuticals and other medicaments, on the human skin are extremely inadequate. Obviously, it is impossible to test potentially toxic and harmful agents directly on human subjects. Even when human subjects are used, difficulties are encountered in obtaining accurate results since researchers must rely on urine or blood samples which reflect the state of the overall individual rather than the state of an isolated area of skin.

Some investigators have attempted, therefore, to substitute laboratory animals for human subjects. However, results obtained using animal skin are not necessarily analogous to those which would be obtained using human skin because of the substantial differences between human and animal skin.

Other researchers have attempted to use dead human skin to measure transdermal flux and similar properties. Dead skin also produces less than satisfactory results. One major factor missing in dead skin is the substantial blood flow normally present in living skin. As a result, existing testing methods, apparatus, and procedures have produced only questionable results.

The present invention overcomes the problems previously encountered by providing the investigator with a living human skin surface. This is done without directly involving a human subject. Furthermore, the present invention provides the researcher with the opportunity of testing blood which directly accesses the affected skin, as opposed to general systemic blood.

As discussed above, according to the present invention, a skin flap is produced on the test animal and this flap can be used as a testing model for medicaments and other substances. In a preferred embodiment of the present invention, the skin flap has human skin on one side and animal skin on the opposite side.

It has been found that congenitally athymic rats are a desirable test animal species. Athymic rats are especially desirable because they are generally hairless (nude). In addition, their athymic state generally renders them less capable of rejecting the human skin implant. Other athymic species may also be used. For example, athymic mice have been employed in some experiments. However, athymic mice have generally been found to have low survival rates and are smaller than would be desired. It will nevertheless, be appreciated that for certain purposes other animals may be used in accordance with the present invention.

While it may be possible to construct skin flaps of the type described at numerous locations on the animal, it has been found that the lower abdomen is an acceptable site. Generally, the lower epigastric region is ideal for the production of a skin flap. This region provides a reliable vascular island which can be easily isolated. Specifically, it is found that using the lower abdominal region provides a vascular island served by the superficial epigastric artery and vein. The vessels utilized to supply the flap are, in athymic rats, consistently about 1 mm in diameter.

According to the present invention, an area of skin located generally in the lower abdomen, and served by the superficial epigastric artery and vein, is isolated. This may be accomplished by making incisions along three sides of a square or rectangular area of the abdomen. Simultaneously, a similarly configured quantity of viable human skin is obtained. A split-thickness skin graft ("STSG") of this skin is formed using known and commonly accepted technology. Specifically, viable skin is harvested and trimmed to an appropriate thickness with a dermatome. Skin is harvested from fresh cadavers within 24 hours of death, or from surgical remnants. In either case, the skin is taken while still viable.

Once the human STSG is obtained and the abdominal area of the test animal is isolated, the human STSG is grafted to the subcutaneous surface of the isolated area of animal skin, so that the vascular pedicle is sandwiched between the human and animal skin layers. This forms a skin flap which then exists essentially as a neurovascular island. This step in the procedure can be more fully appreciated with reference to FIG. 1(a). That figure illustrates the subject area of rat skin as well as the human STSG.

Figure 1:
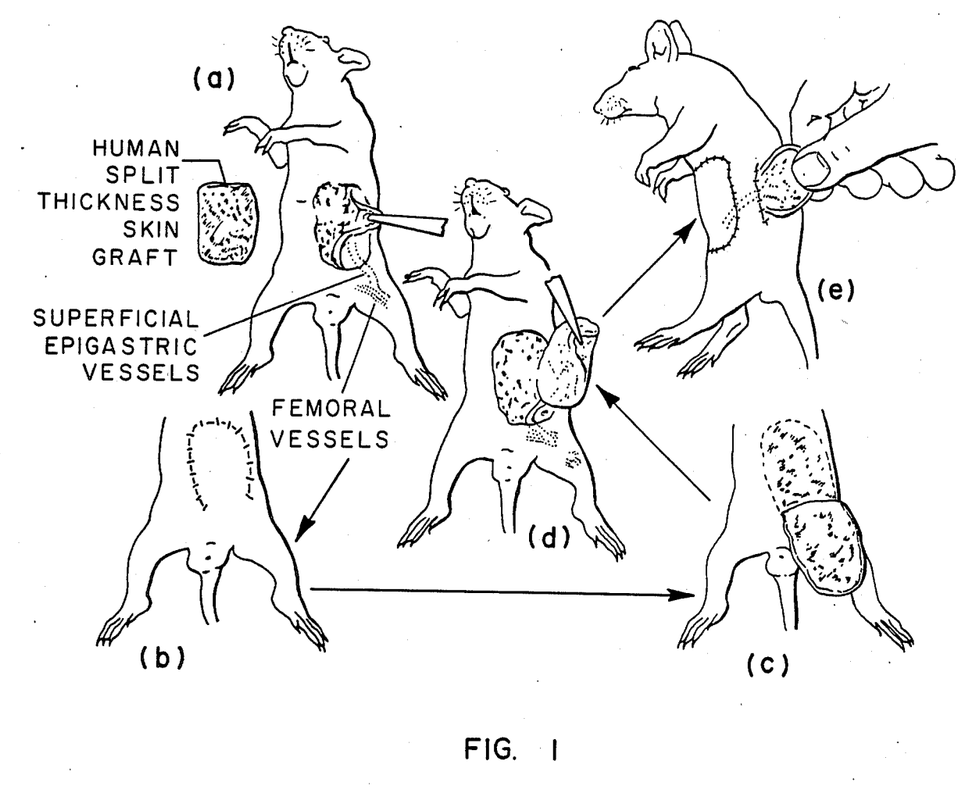
FIG. 1 is a schematic illustration of the various steps in producing the testing model which is the subject of the present invention.

Once the human STSG is grafted in place on the subcutaneous surface of the animal skin, the flap is preferably replaced on the abdomen of the animal. This stage is generally illustrated in FIG. 1(b). At this stage, the dermis of the donor human skin and the subcutaneous tissue of the host island flap grow together. This results in permanent sandwiching of the vasculature supplying the flap between the two skin layers.

Following the surgical procedure described above, the resulting flap receives essentially all of its blood from the epigastric vessels. The result is an effective neurovascular island. Histology has shown that within approximately two weeks, the subcutaneous vessels of the host skin establishes a vascular network with the underlying human STSG. Once the flap is isolated on its neurovascular pedicle, the donor site on the animal's abdomen may be covered by a rat STSG from another animal. This rat STSG is simply sutured in place over the donor site.

In a preferred embodiment of the present invention, a further surgical procedure occurs after approximately two weeks. At this point in time, the femoral vessels distal to the origin of the superficial epigastric vessels are surgically isolated and divided. This procedure results in maximum blood flow from the femoral artery to the flap.

The flap is then raised and totally isolated on its neurovascular pedicle. This procedure is illustrated in FIGS. 1(c) and 1(d). As mentioned above, this pedicle generally is comprised of a single artery, vein, and nerve. Once isolated and raised on its pedicle, the flap is available for use in testing medicaments and other chemical substances.

It has been found desirable, however, to move the flap from this abdominal region in order to provide increased accessibility for testing and to provide decreased chance of damage to the flap due to scratching by the testing animal. Therefore, the flap may be moved to the rat's dorsum by way of a subcutaneous tunnel. This procedure is generally illustrated in FIG. 1(e). This procedure generally involves generating a tunnel subcutaneously via blunt dissection and an accompanying incision at the attachment site on the back of the animal. The flap is then moved through the tunnel, exteriorized through the incision, and sutured in place on the back of the animal.

It will be appreciated that in order to approximate the in situ state of human skin it is necessary to approximate the in situ rate of blood flow through the human skin portion of the flap. Experimentation has shown that the blood flow in the flap does in fact approximate normal blood flow through the skin.

Assessment of blood flow to the flap has been measured with an electromagnetic blood flow transducer which was attached to the isolated femoral artery or vein immediately proximal to the origin of the superficial epigastric vessels. Data shows that the volume of blood flow to and from the flap changes very little with respect to the age of the flap. Typically, the blood flow to the flap was found to be between 1 and 2 ml/min. Since blood flow into and blood flow out of the flap were the same, and because the area of the flap can be determined, blood flow can be stated as volume/time or as volume/area/time. This provides for a greatly increased level of experimental control.

To prevent the need for a collateral blood supply to the flap, tissue anoxia is avoided throughout the surgical procedures used to generate the flap. Blood supply to and drainage from the flap via routes other than the anatomically defined superficial epigastric/femoral system have been found to be minimal.

The lack of a significant collateral blood flow to the flap has been confirmed by the intra-arterial injection of India ink and by the intravenous injection of fluorescein. Injection of India ink into the femoral artery results in homogeneous darkening of both sides of the flap with nearly undetectable amounts of ink finding its way into the skin surrounding the base of the flap.

Following an intravenous injection of fluorescein, the amount of fluorescein that moves into tissue, and the rapidity with which it clears, depends upon the volume of blood to the area, the adequacy of venous drainage, and renal clearance. The influx and clearance of fluorescein, as measured with a surface hand-held dermofluorometer, has been evaluated as a function of time after occluding either the supplying artery or the draining vein.

Occlusion of the vein draining the flap after fluorescein was injected, resulted in a dramatic decrease in the clearance of fluorescein. Likewise, occlusion of the artery supplying the flap resulted in a near total failure of clearance of fluorescein from the flap. Relief of occlusion led to a prompt clearance of flouroscein from the flap. Occlusion of the artery before injection results in a failure of the appearance of fluorescein in the flap. This procedure provides confirmation of the fact that circulation through the flap is virtually exclusive by way of the isolated vascular pedicle described above.

While it is likely that there is some collateral circulation, apparently the prevention of anoxia during the development of the flap, and the healing which occurs between the flap and the rat's body, effectively prevent the development of significant collateral circulation with nondefined vascular components. Further, the dramatic changes seen with the influx and clearance of fluorescein in the various occlusion experiments are supportive of this assumption. The failure to visualize necrosis on the flap every time there is complete occlusion of the supplying vessels implies that the metabolic needs of the skin can be met with very low rates of blood flow and there there may be an unmeasurable low level collateral blood supply to at least some of the flaps.

Microcirculation, primarily of the capillary bed in a rat/rat flap of the type described above, has been analyzed by laser Doppler velocimetry ("LDV"). LDV provides a noninvasive method of assessment of microcirculation within the skin flap. The output signal of this instrument is linearly related to the velocity of red blood cells flowing through the skin.

Changes in the microcirculation of the rat/rat skin flap as it matured, were investigated using the LDV on the skin flap at various time intervals. These time intervals included immediately after transpostion of the flap to the dorsum of the animal, and at intervals of two days, one week, two weeks, three weeks, three months, and five months after transposition. LDV values were taken at four locations across the flap, proximal to distal. Analysis of these data demonstrated that blood flow velocity in the host side of the flap one day after transposition is about 88% of the contralateral, nonsurgically manipulated skin and the blood flow velocity on the grafted side is approximately 80% of normal. These values changed very little as the flap matures in tests done up to five months following transposition.

A similar analysis of a rat/human skin flap has been made. These experiments have been performed throughout the acute stages of the flap development. Following the surgical procedure and raising the flap from its bed, host skin LDV values were not significantly higher than the graft side, either immediately or throughout the next 13 days. Likewise, there was no change in the 14 days after the flap was moved to the back of the animal. The failure to observe a significant collateral blood supply, as well as a lack of variation in the velocity of blood flow supports the conclusion that blood flow to the flap is representative of blood flow in the in situ situation.

To summarize the procedure used to produce the testing model of the present invention, an athymic testing animal, such as an athymic rat, is obtained. An area of the animal's abdomen is identified. In particular, the lower epigastric region is found to be a desirable site. Incisions are then made along three sides of a rectangular or square area on the rat's abdomen to define a skin flap.

The skin flap is formed so that it is served by a defined set of vasculature. Generally, it is desirable to have the flap served by a single artery, vein, and nerve.

A STSG of skin is simultaneously prepared. In one preferred embodiment of the present invention, the STSG is prepared from discarded human skin. The STSG may, however, be skin from other animals depending on the expected use of the invention.

The STSG is then grafted to the subcutaneous surface of the isolated flap of rat skin. Once this procedure has been completed, the resulting flap is returned to its original position on the rat's abdomen, and sutured in place.

After an appropriate period of healing, the flap is again isolated. This involves removing the flap from the abdomen and raising it on its vascular pedicle. Once the flap has been raised, the donor site on the abdomen is covered by another STSG.

It has been found desirable to move the flap to the dorsum of the rat once it has been isolated. This involves transporting the flap through a subcutaneous tunnel and isolating the flap on the back of the animal. This step is taken in order to make the flap more accessible and to prevent damage to the flap which could otherwise occur with the flap isolated below the animal's abdomen.

Once the flap is isolated on the animal, it can be used for testing the effects of pharmaceuticals, cosmetics and chemicals of all types on the skin. The substance to be tested may be introduced by simple surface application. Application using a half-cell diffusion chamber, or by more complex methods of surface application such as iontophoresis.

Periodic blood samples may be taken from the blood vessels accessing the flap. From analysis performed on the extracted blood, the extent of the presence of the substance to be tested can be determined. From this data it is possible to determine the effectiveness of surface application techniques as well as the effects of various substances in contact with the skin. In addition, tests using this model demonstrate the differences between human and rat skin, the importance of microcirculation, and that pharmaceuticals metabolized in the skin may diffuse back to the surface.

EXAMPLES

The following examples are provided in order to illustrate the present invention and are not to be construed as limiting the scope of the present invention or as being inclusive of all embodiments of the invention.

EXAMPLE 1

Breeding pairs of nude rats were obtained from the Animal Production Facility of the National Cancer Institutes (Frederick, MD) and the colony was expanded by mating male rats homozygous for nude (athymic) with females heterozygous for nude.

Intraperitoneal ketamine (Ketaject 100 mg/ml, Parke Davis, Morris Plains NJ), 100 mg/kg of body weight, was used for anesthesia.

Instrumentation used included: (1) Dermatome (Brown Electro-Dematome, Model 666, Zimmer Inc., Warsaw, IN) to generate the split-thickness skin grafts; (2) an operating microscope (Model OPMI 6-SD Carl Zeiss, West Germany) equipped with a fiberoptic illuminator (Model 310187, Dyonics, Andover, MA), to isolate the microvasculature supplying the skin flap; (3) Laser Doppler flow velocimeter (LD 5000, Med Pacific, Seattle, WA)—to noninvasively assess microcirculation of the skin; (4) electromagnetic blood flow transducer, C type 0.5 mm, 0.8 mm, and 1 mm in diameter (C&C INstruments, Culver City, CA)—to directly assess blood flow through the vessels supplying and draining the flap; and (5) a hand-held fiberoptic dermofluorometer (Fluoroscan-Santa Barbara Technology, Santa Barbara, CA), to assess blood flow by monitoring the appearance and clearance of fluorescein in the flap.

Rat split-thickness skin grafts (STSG) (0.3-0.5 mm) were generated from the dorsal skin of sacrificed nude rats. Human STSG (0.3-0.5 mm) were generated from the routinely discarded skin from elective abdominoplastic surgery. The rat and human STSG were either used immediately or stored in RPMI-1640 with 10% bovine serum at 4° C. for up to 72 hours or until used for grafting.

A skin flap was generated by incising the abdominal skin of the rat along three sides. The donor STSG was trimmed to approximate the size of the epigastric flap and was placed in the wound, with the epidermis facing the abdominal musculature of the host. The overlying epigastric host skin was returned to its normal anatomic position. The epigastric skin and the STSG were sutured in place, creating a sandwich having a vascular pedicle sandwiched between the skin layers. This surgical procedure produced a flap which received essentially all of its blood from the superficial epigastric vessels. Histology showed that following a 2 week interval, the subcutaneous vessels of the host skin establish a vascular network with the underlying STSG.

Two weeks later, the femoral vessels distal to the origin of the superficial epigastric vessels were surgically isolated and divided. This manipulation maximized the blood flow from the femoral artery to the sandwich flap. The flap was raised and isolated on its neurovascular pedicle (a single artery, vein, and nerve) using the operating microscope.

The donor site on the rat's abdomen was covered with a STSG from another syngeneic animal and sutured in place. The flap, on its isolated vascular pedicle, was moved through a subcutaneous tunnel to the rat's dorsum, where it was sutured in place.

Since most nude rats will slowly reject human skin grafts, the rat was provided with an injection of cyclosporine (Sandoz, East Hanover, NJ) subcutaneously, 25 mg/kg/day, for 21 days.

This procedure produced a testing model which was useful in performing a wide variety of testing of the effects of various chemical substances, including pharmaceuticals, on skin.

EXAMPLE 2

In this example, the procedure followed in Example 1 was followed to produce a rat/rat skin flap with accessible vasculature.

Test compounds were applied to either the host or the graft side of the flap. Test compounds in their vehicles were placed in either a 1.5 cm diameter well, prepared from a HolliSeal ® skin barrier (a sheet of silicone material with adhesive on both sides) (Hollister Incorporated, Libertyville, IL), or in a half-cell diffusion chamber. The HolliSeal well is generally covered with Parafilm to prevent evaporation. The half-cell diffusion chamber has a 2.7 ml volume, an impeller to avoid problems of unstirred solutions, a water jacket to maintain a constant temperature, and a sampling port (Dependable Scientific Glass, Salt Lake City, UT).

In an initial series of experiments $^{14}C$ benzoic acid, specific activity 58.6 mCi/mM (New England Nuclear, Boston MA) in phosphate buffered saline, was used in various concentrations in the HolliSeal well and the half-cell diffusion chamber. These experiments were designed to compare the absorption of benzoic acid across the host and graft sides of the flap as a means of validating the system. In another series of experiments 3H-vidarabine, specific activity 38 mCi/mg (2.7 ml), was added to a half-cell diffusion chamber to validate the flap as a system to study the metabolism of a drug as it crosses the skin. 3H-vidarabine, specific activity 38 mCi/mg (2.7 ml), was added to a half-cell diffusion chamber attached to rat/rat skin sandwich flaps, which had previously been tape-stripped.

At the time of an experiment, with the animal under Ketamine anesthesia, the vessels supplying and draining the flap were exposed through an incision over the inguinal ligament. A venotomy was made in the femoral vein proximal to the juncture of the superficial epigastric vein to sample flap blood. A venotomy was also made in the contralateral femoral view to sample systemic blood. The blood samples (approximately 40 ul) were collected periodically in heparinized microhematocrit capillary tubes. Concentration of radiolabeled compound, or its metabolities, in the blood were subsequently assessed by liquid scintillation counting and chromatographic techniques. Concentrations in the donor chamber were sampled periodically and quantitated in a similar manner.

To compare absorption across the graft vs. the host side of the rat/rat flap, $^{14}$benzoic acid, 0.52 uCi/ul in unbuffered water, 100 ul total volume was placed in the HolliSeal ® well on either the host side or the graft side of the flap. Aliquots of flap blood, as well as systemic blood, were collected at 5–10 min. intervals, and analyzed for the concentration of benzoic acid with a liquid scintillation counter. Peak flux across host skin occurred at 30 minutes and then decreased rapidly. Assuming a blood flow of 1.5 ml/min, flux of benzoic acid across host skin was calculated to be 0.84 uCi/min/cm$^2$. The same experiment across the grafted side, three weeks later, demonstrated a peak flux of 2.2 uCi/min/cm$^2$ with an even more rapid decline. While the flux was greater across the grafted side, the total amount absorbed was the same, 1.04 min.ug/ul. The decrease in benzoic acid concentration in the donor well was linear with time, decreasing from 2.2 ug/ml to 0.75 ug/ml. These experiments suggested that the concentration of benzoic acid was the driving force for the transdermal absorption of benzoic acid.

Additional experiments, using an antiviral substance, vidarabine, have been performed to assess the metabolic activity in the skin. It is known that vidarabine is metabolized by an enzyme in the skin, deaminase. Accordingly, radiolabeled vidarabine was placed on a rat/rat skin sandwich flap system, and the amount of vidarabine and its metabolite, ara-H, was measured in the blood draining the flap. Ara-H also diffused back through the skin into the donor chamber. These data demonstrate that the model system can be used to assess metabolic capabilities of the skin. The back-diffusion of ara-H suggests that the system can be used to determine the flux of systemically delivered drugs into the epidermis and stratum corneum.

EXAMPLE 3

In this example the experimental procedure described in Example 1 was followed. A rat/human flap was prepared using an identical procedure.

In this experiment, 20 ug of $^{14}$C benzoic acid (4.5 uCi) in 95% ethanol was applied to the host side of the flap. In this vehicle, peak flux was seen in one hour. Thereafter steady state was attained and flux was calculated to be 0.045 uCi/min/cm$^2$. An additional experiment was performed where the same amount of benzoic acid was applied in a half-cell diffusion chamber, i.e., whose hydration of the skin was maintained at a maximal state. In this setting, peak flux occurred within 10 minutes. These data effectively validated the system as being useful for determining transdermal flux and the influence of vehicle on flux in human skin.

EXAMPLE 4

In this example the experimental procedure described in Example 1 was followed and a rat/rat flap was prepared using an identical procedure. The purpose of this example is to illustrate the role of blood flow on percutaneous absorption processes. In this example, blood flow was locally altered by iontophoresis of phenylephrine. Following the establishment of decreased microcirculation in a circumscribed area, benzoic acid was applied to the treated area. The experiment was repeated two weeks later in a nontreated mode, i.e., no alteration in the microcirculation. Repeat analysis of this type of approach demonstrates that peak benzoic acid levels do not appear in flap blood until approximately 140 minutes. In the situtaton where there is no alteration in the mircocirculation, peak levels occur in approximately 10 minutes. There results reveal that in situations, where compounds are rapidly absorbed, microcirculation to the skin is of critical importance.

EXAMPLE 5

ZIn this example experimental proecdure described in Example 1 was followed and a rat/human flap, as well as a rat/rat flap, were prepared using an identical procedure. The objective of this experiment was to determine differences in absorption, rat skin vs. human skin, rat graft vs. rat host skin, with a second agent, caffeine. Application of caffeine in a teflon well attached to either host rat graft or human graft displayed absorption curves that are similar in kinetics. However, rat skin permits approximately an 8-fold increase in absorption, relative to human skin. These data demonstrate that rat skin is quite dissimilar from human skin relative to percutaneous absorption.

EXAMPLE 6

Compounds will frequently bind to the skin. Thus, after being absorbed through the outer protective layer, the stratum corneum, there is a possibility that the compound being tested will not be absorbed into the blood stream. It is anticipated that caffeine could be such a product. In in vitro experiments, it has been demonstrated that caffeine, when topically applied to human skin, does not appear in the donor chamber until 6–12 hours after application. It is surprising to observe peak levels of caffeine within 30 minutes of topical application in the in vivo situation using the system described in Example 1. Repeat experiments with caffeine show that: (a) there are binding sites within the lower layer of skin which bind caffeine. Because no blood circulates through this in vitro, there is necessarily a considerable delay in the time that caffeine takes to reach the microcirculation and hence its transportation to the rest of the body; (b) this was confirmed by adding a second dose of caffeine in vitro and in vivo and comparing the absorption profiles. In the in vitro setting, adding two doses did not alter absorption, whereas in the in vivo setting, there was a greater than predicted absorption. This confirmed the notion that there are binding sites of caffeine within the dermis.

These experiments demonstrate the difference between rat and human skin and the dramatic differences between in vitro and in vivo experiments in human skin.

In summary, the present invention provides an experimental model and methods for its use in determining the behavior of chemical substances in contact with living human skin. This is accomplished without the use of human subjects and is accomplished in such a manner that samples of the blood directly accessing the human skin can be easily obtained and analyzed. This provides data which is extremely accurate and valuable when compared with data obtained using existing methods.

The present invention will be useful in obtaining an understanding of the details of the functions of the human skin. Specifically, an increased understanding of the behavior of the skin in what is essentially an in vivo setting can be obtained using the present invention. Data obtained to date has demonstrated dramatic differences between rat and human skin, the importance of microcirculation in percutaneous absorption, and that drugs which are metabolized in the skin tend to diffuse back to the surface.

Additional desirable features of the present invention include: (1) the ability to monitor systemic blood levels as a function of levels in the flap blood; (2) the ability to monitor the disappearance of test compounds from a donor chamber; and, thus, (3) the ability to accurately measure transdermal flux.

A wide range of possible uses of the present invention can be easily identified. Some of these uses may include: (1) studying the interaction of the skin with toxic substances; (2) studying the metabolic capacity of the skin; (3) studying the skin as a barrier to drug delivery; (4) studying blood flow and environmental factors; (5) studying the delivery of systemic drugs to the skin; (6) studying the metabolism of natural hormones, cytokines or drugs within the skin; and (7) studying the inflammatory processes. The ability to make the studies outlined above opens new areas of medical science not previously available for detailed analysis.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced with their scope.

What is claimed and desired to be secured by United States Letters Patent is:

1. A method for testing the effects of substances on human skin comprising the steps of:
   (a) providing an isolated skin flap having a layer of living human skin and a layer of living animal skin, said flap being served by an isolated vasculature attached to a test animal and sandwiched between the layers of skin such that substantially all blood leaving the flap flows through the isolated vasculature;
   (b) placing a quantity of the substance to be tested in contact with the human skin portion of the skin flap;
   (c) removing at least one sample of blood from the isolated vasculature as the blood leaves the skin flap;
   (d) analyzing the contents of the blood removed.

2. A method as defined in claim 1 wherein the test animal is athymic.

3. A method as defined in claim 2 wherein the animal is a mouse.

4. A method as defined in claim 2 wherein the animal is a rat.

5. A method as defined in claim 1 wherein the layer of animal skin is located on the abdomen of the test animal.

6. A method as defined in claim 5 wherein the layer of animal skin is located in the inferior epigastric region.

7. A method as defined in claim 1 wherein a half-cell diffusion chamber is used to apply the substance to be tested to the skin flap.

8. A method as defined in claim 1 wherein the substance to be tested comprises a drug.

9. A method as defined in claim 1 wherein the substance to be tested comprises a toxic substance.

10. A method as defined in claim 1 wherein the substance to be tested comprises a carcinogen.

11. A method as defined in claim 1 wherein the substance to be tested is applied to the skin flap using iontophoresis.

12. A method as defined in claim 1 wherein the substance to be tested comprises a cosmetic.

13. A method for testing the effects of substances on human skin comprising the steps of:
   (a) obtaining a split thickness skin graft of human skin;
   (b) isolating an area of the skin of a test animal such that the isolated area of skin forms a neurovascular island attached to the animal;
   (c) grafting the human skin graft to the subcutaneous surface of the isolated area of skin on the test animal in order to form a skin flap having human skin on one surface and animal skin on the other surface;
   (d) reimplanting the skin flap into the test animal for a sufficient period of time that the split thickness skin graft and the isolated area of animal skin grow together;
   (e) after the split thickness skin graft and animal skin have grown together, as described in step (d), raising the flap on the neurovascular island so as to isolate the vasculature which serves the resulting skin flap;
   (f) placing a quantity of the substance to be tested in contact with the skin flap;
   (g) removing at least one sample of blood from the isolated vasculature as the blood leaves the skin flap;
   (h) analyzing the contents of the blood removed.

14. A method as defined in claim 13 wherein the test animal is athymic.

15. A method as defined in claim 14 wherein the animal is a mouse.

16. A method as defined in claim 14 wherein the animal is a rat.

17. A method as defined in claim 13 wherein the isolated area of skin is located on the abdomen of the test animal.

18. A method as defined in claim 17 wherein the isolated area of skin is located in the inferior epigastric region.

19. A method as defined in claim 13 wherein the test animal is treated such that rejection of the split thickness skin graft is prevented.

20. A method as defined in claim 19 wherein the test animal is given cyclosporine.

21. A method as defined in claim 17 further comprising the step of transpositioning the skin flap to the dorsum of the test animal.

22. A method as defined in claim 21 wherein the skin flap is transpositioned to the dorsum of the test animal by way of a subcutaneous tunnel.

23. A method as defined in claim 13 wherein the substance to be tested is placed on the human skin surface.

24. A method as defined in claim 13 wherein a half-cell diffusion chamber is used to apply the substance to be tested to the skin flap.

25. A method as defined in claim 13 wherein the substance to be tested comprises a drug.

26. A method as defined in claim 13 wherein the substance to be tested comprises a toxic substance.

27. A method as defined in claim 13 wherein the substance to be tested comprises a carcinogen.

28. A method as defined in claim 13 wherein the substance to be tested comprises a cosmetic.

29. A method for producing a neurovascular island skin flap on an athymic test animal comprising the steps of:
  (a) obtaining a split thickness skin graft of skin;
  (b) isolating an area of the skin of the test animal on the abdomen of the test animal such that the isolated area of skin forms a neurovascular island attached to the animal comprising the superficial epigastric vessels;
  (c) grafting the split thickness skin graft to the subcutaneous surface of the isolated area of the animal's skin in order to form a skin flap; and
  (d) isolating the vasculature which serves the skin flap.

30. A method as defined in claim 29 wherein the animal is a mouse.

31. A method as defined in claim 29 wherein the animal is a rat.

32. A method as defined in claim 29 wherein the split thickness skin graft comprises human skin.

33. A method as defined in claim 29 wherein the test animal is treated such that rejection of the split thickness skin graft is prevented.

34. A method as defined in claim 33 wherein the test animal is injected with cyclosporan.

35. A method as defined in claim 29 further comprising the step of transpositioning the skin flap to the dorsum of the test animal.

36. A method as defined in claim 35 wherein the skin flap is transpositioned to the dorsum of the test animal by way of a subcutaneous tunnel.

* * * * *

UNITED STATES PATENT AND TRADEMARK OFFICE
CERTIFICATE OF CORRECTION

PATENT NO. : 4,677,968

DATED : July 7, 1987

INVENTOR(S) : Gerald G. Krueger

It is certified that error appears in the above-identified patent and that said Letters Patent are hereby corrected as shown below:

Title Page, Col. 1, 3rd line under "References Cited": "Congentially" should be -- Congenitally --

Title Page, Col. 2, (the line opposite "PUBLICATIONS"): "Maintainence" should be -- Maintenance --

Col. 1, line 41, "skin in an" should be -- skin is an --

Col. 2, line 17, "using human subject" should be -- using human subjects --

Col. 2, line 35, "differences hair density" should be -- differences in hair density --

Col. 5, line 66, "then" should be -- them --

Col. 7, line 60, "Occulsion" should be -- Occlusion --

Col. 7, line 60, after "flap" insert comma

Col. 7, line 66, "Occulsion" should be -- Occlusion --

Col. 8, line 10, "occulsion" should be -- occlusion --

UNITED STATES PATENT AND TRADEMARK OFFICE
CERTIFICATE OF CORRECTION

PATENT NO. : 4,677,968

DATED : July 7, 1987

INVENTOR(S) : Gerald G. Krueger

It is certified that error appears in the above-identified patent and that said Letters Patent is hereby corrected as shown below:

Col. 9, line 65, "INstruments" should be -- Instruments --

Col. 11, line 19, "metabolities," should be -- metabolites, --

Col. 12, line 25, "There" should be -- These --

Col. 12, line 26, "situations, where" should be -- situations where --

Col. 12, line 30, "ZIn" should be -- In --

Col. 12, line 30, "proecdure" should be -- procedure --

Signed and Sealed this

Fifteenth Day of December, 1987

*Attest:*

DONALD J. QUIGG

*Attesting Officer*   *Commissioner of Patents and Trademarks*